United States Patent [19]

Rheaume et al.

[11] Patent Number: 5,560,909
[45] Date of Patent: Oct. 1, 1996

[54] INSECTICIDAL COMPOSITIONS AND PROCESS FOR PREPARATION THEREOF

[75] Inventors: Lisa J. Rheaume, Midland, Mich.; Julia A. Gegner, Eugene, Oreg.; James J. Jakubowski, Midland, Mich.; Daniel H. Haigh, Sanford, Mich.; James Peters, Midland, Mich.

[73] Assignee: DowElanco, Indianapolis, Ind.

[21] Appl. No.: 736,535

[22] Filed: Jul. 26, 1991

Related U.S. Application Data

[63] Continuation of Ser. No. 311,662, Feb. 16, 1989, abandoned, which is a continuation-in-part of Ser. No. 870,195, Jun. 3, 1986, abandoned.

[51] Int. Cl.$^6$ .......................... A01N 63/00; A01N 25/00; A01N 25/34; C12N 1/20
[52] U.S. Cl. ................. 424/93.1; 424/93.1; 424/93.16; 424/93.461; 424/93.6; 424/405; 424/408; 435/182; 435/252.31; 435/524; 435/252.5; 435/822; 435/832; 435/948; 514/972
[58] Field of Search ............................ 435/182, 252.31, 435/832, 252.5, 252.1, 822, 948; 424/93 B, 93 D, 405, 408, 93 K, 93.461, 94.46, 93.4, 93.6, 93.1; 514/972, 89

[56] References Cited

U.S. PATENT DOCUMENTS

| | | | |
|---|---|---|---|
| 29,933 | 3/1879 | George et al. | 424/78 |
| 2,652,322 | 1/1953 | Hedrick | 71/2.7 |
| 3,212,967 | 10/1965 | McFadden et al. | 167/42 |
| 3,228,830 | 1/1966 | McFadden et al. | 167/42 |
| 3,400,093 | 9/1968 | Feinberg | 260/29.6 |
| 3,541,203 | 11/1970 | Fogle et al. | 424/17 |
| 3,590,119 | 6/1971 | Cardarelli et al. | 424/22 |
| 3,660,071 | 5/1972 | Gould | 71/65 |
| 3,660,563 | 5/1972 | Gould et al. | 424/81 |
| 3,767,790 | 2/1972 | Guttag | 424/81 |
| 3,842,022 | 8/1973 | Wang | 260/17.4 |
| 3,962,038 | 6/1976 | Kawashima et al. | 435/182 |
| 3,984,541 | 10/1976 | Letchworth et al. | 514/972 |
| 4,018,594 | 4/1977 | Blank | 71/97 |
| 4,021,364 | 5/1977 | Speiser et al. | 252/316 |
| 4,056,610 | 11/1977 | Barber, Jr. et al. | 424/32 |
| 4,061,466 | 12/1977 | Sjohölm et al. | 435/182 |
| 4,076,516 | 2/1978 | Vartiak | 71/66 |
| 4,194,066 | 3/1980 | Kaetsu et al. | 435/182 |
| 4,250,163 | 2/1981 | Nagai et al. | 424/14 |
| 4,282,209 | 8/1981 | Tocker | 424/81 |
| 4,286,020 | 8/1981 | Himel | 428/407 |
| 4,303,642 | 12/1981 | Kangas | 424/78 |
| 4,304,591 | 12/1981 | Mueller et al. | 71/93 |
| 4,304,769 | 12/1981 | Chen | 424/218 |
| 4,328,203 | 5/1982 | Spence et al. | 424/16 |
| 4,343,790 | 8/1982 | Pasarela | 424/81 |
| 4,353,962 | 10/1982 | Himel et al. | 428/407 |
| 4,370,313 | 1/1983 | Davies | 424/32 |
| 4,394,287 | 7/1983 | Scarpelli | 64/4.32 |
| 4,434,228 | 2/1984 | Swann | 435/182 |
| 4,435,383 | 3/1984 | Wysong | 424/78 |
| 4,460,572 | 7/1984 | Derby et al. | 424/78 |
| 4,461,759 | 7/1984 | Dunn | 424/19 |
| 4,470,966 | 9/1984 | Costanza et al. | 424/81 |
| 4,647,536 | 3/1987 | Mosbach et al. | 435/177 |
| 4,744,933 | 5/1988 | Rha et al. | 264/4.3 |
| 4,765,982 | 8/1988 | Ronniny et al. | 424/403 |
| 4,791,061 | 12/1988 | Sumino et al. | 435/178 |
| 4,810,793 | 3/1989 | Kozuma et al. | 514/89 |
| 4,844,896 | 7/1989 | Bohm et al. | 424/89 |
| 4,948,586 | 8/1990 | Bohm et al. | 424/106 |
| 4,983,389 | 1/1991 | Levy | 424/404 |
| 4,985,251 | 1/1991 | Levy | 424/404 |
| 5,283,060 | 2/1994 | Shieh | 424/93 L |
| 5,286,495 | 2/1994 | Batich et al. | 424/490 |

FOREIGN PATENT DOCUMENTS

| | | | |
|---|---|---|---|
| 846785 | 7/1970 | Canada | 167/9 |
| 0145087 | 7/1985 | European Pat. Off. . | |
| 628312 | 5/1981 | Israel . | |

OTHER PUBLICATIONS

J. Margalit et al., "Effect of Encapsulation on the Persistence," Appl. Microbiol Biotechnol (1984) 19:382–383.

A. Aronson et al., "Bacillus Thuringiensis and Related Insect Pathogens," Microbiological Reviews, Mar. 1986. pp. 1–24.

J. Hoover, "Alkali–Dispersible Ethylene–Acrylic Acid Copolymers for Pigmented Coatings," Tappi, Feb. 1971, vol. 54, No. 2, pp. 257–261.

Margalit, J. et al., "Appl. microbiol. Biotechnol." vol. 19, pp. 382–383, 1984.

*Primary Examiner*—Michael G. Wityshyn
*Assistant Examiner*—K. Larson
*Attorney, Agent, or Firm*—D. Wendell Osborne; S. Preston Jones

[57] ABSTRACT

The invention concerns certain insecticidal compositions of ingestible insecticides selected from the group consisting of DNA viruses, RNA viruses and bacteria of the order *Bacillus* such as, for example, *Bacillus thuringiensis* var. *israelensis* entrapped by a suitable charged polymer. The invention also concerns a process for the preparation of and the use of such insecticidal compositions.

62 Claims, No Drawings

INSECTICIDAL COMPOSITIONS AND PROCESS FOR PREPARATION THEREOF

CROSS REFERENCE TO RELATED APPLICATION

This application is a continuation of application Ser. No. 07/311,662, filed Feb. 16, 1989, now abandoned, which is a continuation-in-part of application Ser. No. 06/870,195, filed Jun. 3, 1986, now abandoned.

BACKGROUND OF THE INVENTION

There is considerable commercial interest in insecticidal compositions which exhibit insecticidal activity against target insects after the composition has been ingested by the target insect, especially ingestable biological insecticides. Microorganisms such as viruses and bacteria and certain products made by or within bacteria are examples of ingestible biological insecticides currently used to combat insect pests. The most widely used ingestible biological insecticide is *Bacillus thuringiensis*, of which many varieties are known, and products made by or within this bacterial species.

Ingestible biological insecticides have several advantages over conventional chemical insecticides such as being relatively nontoxic and nonpathogenic to nontarget organisms such as humans.

Despite the advantages of ingestible biological insecticides, they also have several disadvantages which limit their effectiveness. Among these disadvantages are low stability in the presence of decomposing organic matter and low site persistence. For example, typical commercial products employed to control mosquito larvae containing *Bacillus Thuringiensis* var. *israelensis* and the high density insecticidal crystalline protein produced by this organism are not always effective when used in an aqueous environment to kill and control mosquito larvae because these compositions tend to have high bulk density and often sink in the water to depths below the mosquito larvae feeding zone. In addition, many biological insecticides, for example, *Bacillus thuringiensis*, suffer lowered site persistence due to their instability, which is a result of chemical and/or physical degradation, when exposed to various environmental factors such as ultraviolet light and the like.

In order to increase the site persistence and/or stability of biological insecticides, these insecticides have been adsorbed onto latex beads (see Sehnell, D. J., *Science* ((1984) 223:1191) or encapsulated with lactones (see European Patent Application 145,087) or polyethylene (see Margalit, J. et al., *Appl. Microbial. Biotechnol.* ((1984) 19:382–383).

While encapsulation is effective in meeting some of the above stated goals, many prior art methods of encapsulation involve the use of harsh treatment procedures such as the use of organic solvents and/or heat. Biological insecticides in general are sensitive to such harsh treatments and can lose substantial activity when these encapsulation procedures are employed.

It would be desirable to have a biological insecticidal composition containing a biological ingestible insecticide that has increased stability and site persistence. It would also be desirable to have a process for preparing such insecticidal composition which avoids the use of the aforementioned harsh encapsulation procedures.

The present invention relates to insecticidal compositions of increased persistence and stability and a process for preparation thereof which involves a mild process of entrapment or encapsulation. The process of the present invention can also be applied directly to an aqueous suspension, such as to a fermentation broth or concentrate. The present invention also concerns a method of using the insecticidal compositions described herein for the control of target insects.

SUMMARY OF THE INVENTION

The present invention is directed to a insecticidal composition comprising an insecticidally effective amount of a suitable insecticide selected from the group consisting of DNA viruses, RNA viruses and bacteria of the genus *Bacillus* entrapped by a suitable charged polymer. The charged polymer typically comprises about 5 percent to about 99.999 percent by weight of the polymer/insecticide composition, based on the total weight of the polymer and insecticide.

The insecticidal composition of the present invention has physical characteristics such that it is capable of ingestion by a target insect. The insecticidal compositions can optionally contain other active agents and/or fillers or other additives which enhance the activity of the composition or impart other desirable characteristics to the composition. It is preferred that the insecticidal compositions of the present invention have higher water flotation ability as compared to unencapsulated or unentrapped insecticides.

The present invention also concerns a method of using the insecticidal compositions of the present invention for the control of target insects and is also directed to a process for the preparation of such insecticidal compositions.

As used herein, the term "ingestible insecticidal composition" means a composition which has physical characteristics, such as sufficiently small particle size, that the composition is capable of being ingested by the target insect and that the insecticide contained in the composition exhibits its insecticidal activity after ingestion by the target insect.

The term "insecticide" or "ingestible insecticide" refers to insecticides which exhibit their insecticidal activity after ingestion by the target insect.

The term "insecticidally effective amount" refers to that amount of insecticide that will lead to control of a target insect.

The term "control" refers to inhibition, kill or any other interference which disrupts the normal life processes of a target insect in a manner adverse to the insect.

DETAILED DESCRIPTION OF THE INVENTION

The process of making the insecticidal compositions of the present invention comprises contacting a suitable ingestible biological insecticide with a suitable charged polymer in an aqueous medium, modifying the charge of the charged polymer to cause precipitation of the polymer which entraps the insecticide therein to form a solid insecticidal composition comprised of an insecticidally effective amount of said insecticide and an entrapping amount of said charged polymer. A typical entrapping amount of charged polymer is from about 5 percent to about 99.999 percent by weight of the charged polymer, compared to the total weight of the insecticide and polymer. A preferred amount of charged polymer present in the compositions of the present invention is from about 25 percent to about 99.99 percent by weight;

and a more preferred amount is from about 50 to about 99.9 percent by weight.

Charged polymers are well known in the field of polymer chemistry and are commercially available. Suitable charged polymers useful in the present invention for entrapping the ingestible insecticides are one or more of such charged polymers having the capability of existing in solution or as a dispersion in an aqueous phase and which precipitate from the aqueous phase when the charge is modified.

The term "precipitate" or "precipitation" as used herein means that if the charged polymer is soluble in water, it becomes insoluble upon a charge modification; or if the charged polymer exists as a dispersion in water, it forms aggregates and comes out of suspension upon a charge modification.

As used herein, the term "charged polymer" refers to a polymer bearing functional group that is charged or capable of being charged. Thus, if the charged polymer is an anionic polymer, it will contain functional groups which are predominantly in the acid form, or as a salt of an acid, or as combinations of the acid and salt forms.

Anionic charged polymers may also contain other functional groups, including cationic functional groups; however, the majority of the functional groups will be in the acid form and/or as a salt of an acid.

If the charged polymer is a cationic polymer, it will contain functional groups which are predominantly in the base form, or as a salt of a base, or as combinations of the base and salt forms. Cationic charged polymers may also contain other functional groups, including anionic functional groups; however, the majority of the functional groups will be in the base form and/or as a salt of a base. A key feature of the present invention is that upon precipitation of the charged polymer, the ingestible biological insecticide, becomes entrapped in the precipitated polymer matrix.

The terms "entrapped" and/or "encapsulated" means that the insecticide is in direct association with the charged polymer (that is, entrapped in the polymer matrix not in the liquid phase). Thus, the polymer and the insecticide have a greater affinity for each other than either has for the water phase. This affinity which leads to entrapment may be due, for example, to ionic effects, hydrophobicity, hydrogen bonding, van der Waals forces, or other such physical attraction or covalent or noncovalent chemical bonding.

Suitable charged polymers can be homopolymers, copolymers, multipolymers, or any mixture thereof, bearing functional groups that are charged or capable of being charged. The size, molecular weight and other physical characteristics of the polymers are not critical as long as the polymers can precipitate upon charge modification and entrap the desired insecticide therein.

The functional groups that impart the charge to the charged polymers can be acid derivatives that have a negative charge or are capable of having a negative charge such as carboxylic, sulfonic, phosphonic or phosphinic moieties in the acid form and/or as a salt thereof. In contrast, the functional groups can also be derivatives that have a positive charge or are capable of having a positive charge such as ammonium, sulfonium, phosphonium or pyridinium moieties. It is contemplated that mixtures of functional groups may be present on the polymer or mixtures of polymers; however, the polymer must contain sufficient cationic or anionic functional groups or groups which are capable of becoming anionic or cationic functional groups so that the overall charge of the polymer can be modified.

The number or quantity of functional groups on the charged polymer is only important insofar as the charge allows the polymer to be dispersed in an aqueous medium or in solution in an aqueous medium and said polymer precipitates when the charge is modified and entraps the desired insecticide. Therefore, the quantity of charged functional groups required in the polymer will vary with the type of functional group, the type of polymer, the type of insecticide, and the method of charge modification. For example, if the functional group is a carboxylic acid moiety, the carboxylic acid moiety will typically be between about 4 percent and about 63 percent by weight of the total weight of the polymer, preferably between about 9 percent and about 63 percent.

Suitable anionic charged polymers having carboxylic moieties are linear or cross-linked polymers of acrylic acid, and copolymers or multipolymers of polymerizable alkenes and acrylic acid and/or methacrylic acid, for example, copolymers of ethylene and acrylic acid or ethylene and methacrylic acid. Typical anionic charged polymers that have sulfonic moieties are polystyrene sulfonate and carrageenan, types IV and V. Suitable anionic polymers that have phosphonic or phosphinic moieties are latexes of styrene and butadiene monomers containing phosphinic acid moieties and latexes of styrene-butadiene monomers containing phosphonic acid moieties.

Suitable cationic charged polymers having ammonium moieties are protonated primary, secondary, or tertiary amines such as polymers of ethylenimine; quaternary pendant amines such as polymers of vinylbenzyltrimethylammonium chloride and polymers of diallyldimethylammonium chloride; and quaternary integral amines such as polybrene ioneneo A typical cationic charged polymer that has sulfonium moieties is reactive polysoap (i.e., methyl methacrylate and vinylbenzyl chloride onium derivatized copolymer).

The most preferred polymers for use in the present invention are copolymers of ethylene and acrylic acid monomers or ethylene and methacrylic acid monomers. Also preferred are other acrylic acid copolymers or methacrylic acid copolymers such as those prepared from acrylic and acrylate monomers, and methacrylic and acrylate monomers. The most preferred copolymer is an ethylene and acrylic acid copolymer in which the amount of acrylic acid is from about 10 percent to about 99 percent, by weight, of the total copolymer, preferably between about 12 percent and about 25 percent and most preferably between about 15 percent and about 20 percent by weight. As indicated hereinabove the polymers employed in the present invention are well known, for example, copolymers of ethylene and acrylic acid are taught in Netherland Application No. 6,414, 741 (*Chemical Abstracts,* 63:P 18297h (1965)).

The term "charge modification" refers to the act of modifying the charge of the functional groups of the suitable charged polymer sufficient enough to cause precipitation of the polymer and the entrapment of the insecticide therein. Charge modification of the polymer to effect precipitation of the polymer and entrapment of the insecticide can be accomplished by several means. For example, the pH of the aqueous environment containing the charged polymer can be raised or lowered, depending upon the polymer, to a pH which causes polymer precipitation. The pH can be changed by the addition of an organic acid or mineral acid, for example, acetic acid or HCl or a base such as KOH or NaOH.

Alternatively, the charged polymer can be salted out of solution with simple salts such as KCl or NaCl; or multivalent ions of a charge opposite to the polymer can be added to the aqueous solution to cause precipitation of the charged polymer, for example, $Ca^{++}$, $Al^{+++}$ or $SO_4^{--}$; or the charged polymer can be coacervated with another polymer having an opposite charge. If the charged polymer is neutralized with a volatile ion in order to effect dispersion or dissolution of the polymer (e.g., polymers of ethylene and acrylic acid, ethylene and methacrylic acid, acrylate and acrylic acid, acrylate and methacrylic acid or other polymers or copolymers containing acid functionality, neutralized, for example, with ammonium hydroxide), the biological insecticide can be dispersed in the polymer dispersion or solution, and the charge of the polymer subsequently modified by simple drying procedures that allow the ammonia to volatilize along with the water, thereby placing the polymer in the charge-modified form.

As appreciated by one skilled in the art of polymer chemistry, the specific method selected to cause precipitation of the polymer and entrapment of the insecticide will depend upon factors such as the properties of the polymer used for entrapment and the properties of the insecticide to be entrapped. The efficiency of insecticide entrapment will vary with different polymers and insecticides based on the relative affinities for each insecticide and each polymer.

The ingestible insecticides used in the compositions of the present invention are those insecticides that are insecticidally effective in controlling target insects after the target insects have ingested the insecticidal composition. Typical target insects capable of ingesting the insecticidal compositions of the present invention are arthropod organisms such as spiders, mites, insects and the like, particularly insects of the *Lepidoptera, Diptera, Coleoptera, Orthoptera, Isoptera,* or *Homoptera* orders.

The ingestible biological insecticides for use in the compositions and processes of the present invention are microorganisms, such as viruses and certain bacteria, that are toxic to insects. In addition, insecticidally toxic components of the bacterial microorganisms and insecticidally toxic products of these microorganisms are suitable for use in the present invention.

Suitable ingestible insecticides for use in the compositions of the present invention are microorganisms such as, for example, DNA viruses, particularly entomopoxvirus, irdovirus, baculovirus such as nuclear polyhedrosis virus (NPV) as well as "granulosis" virus (GV); RNA viruses such as cytoplasmic polyhedrosis virus (CPV) and among these, the nuclear polyhedrosis virus is preferred; and bacteria belonging to the genus *Bacillus* which are pathogenic to insects are also suitable ingestible insecticides for use in the compositions of the present invention. These bacteria can be nonsporulating or sporulating organisms. Preferred bacteria are the spore-forming bacteria, and their components and products. Examples of these preferred bacteria include *Bacillus thuringiensis, Bacillus sphaericus, Bacillus popilliae, Bacillus cereus, Bacillus lentimorbus,* and *Bacillus fribourgensis. Bacillus thuringiensis* of all varieties are preferred; particularly preferred are the varieties: thuringiensis; san diego; tenebrionic; kurstaki aizawa and israelensis.

Information concerning biological insecticides and insect pests can be found in *Microbial Control of Pests & Plant Diseases* 1970–1980, H. D. Burges (Ed.), Academic Press, (1981); and Microbiological Reviews, March 1986, pp. 1–24.

As used herein, the term "Bt" means any insecticidally active variant of *Bacillus thuringiensis* and its components and products, and the term "Bti" means *Bacillus thuringiensis* var *israelensis* and its components and products.

As would be apparent to a skilled artisan, the gene(s) or equivalents which express the biological insecticides of the genus *Bacillus*, may readily be inserted and expressed in other microorganisms which are insecticidally inactive prior to transformation. A suitable genetic manipulation technique is taught by E. S. Ward et al., *Federation of European Biochemical Societies* 1820, Volume 175, no. 2, October (1984), pages 377–382.

Exemplary microorganisms in which the gene(s) which are derived from the gene(s) which express the biological insecticides of the genus *Bacillus* may be inserted include, among others, yeast and algae.

By "equivalent" gene(s) is meant to include those gene(s) which are derived from the gene(s) which express the biological insecticides of the order *Bacillus*.

By "derived" it is intended to mean DNA sequences, which are modified into altered forms. By "altered" forms is meant to include the addition, deletion, or nonconservative substitution of a limited number of various nucleotides or the conservative substitution of many nucleotides, provided that the proper reading frame is maintained.

Techniques for substitution at predetermined nucleotide sites having a known sequence are well known. Exemplary techniques include site-directed mutagenesis, the polymerase chain reaction technique, and exon shuffling. Substitution may be conducted by making nucleotide insertions, usually on the order of about 1 to about 10 nucleotides, or deletions of about 1 to about 30 nucleotides. Substitutions, deletions, insertions or any subcombination may be combined to arrive at a final construct.

Moreover, any source of DNA which provides a DNA sequence having a homologous segment to the DNA encoding the gene is now readily within the means of those of ordinary skill in the art. A series of probes, made from genes of all or a part of the gene(s) which express the biological insecticides of the genus *Bacillus*, could be used to find homologous genes or gene segments. By "homologous genes or gene segments" is meant to include any DNA sequence whose mRNA hybridizes with the probes of all or a part of the gene, provided that the homologous segment or homologous genes produce proteins being at least insecticidally equivalent to the biological insecticides produced by the genus *Bacillus*.

The biological insecticides which are entrapped to form the ingestible insecticidal compositions of the present invention can be entrapped in numerous forms, for example, the bacterial microorganisms themselves may be entrapped in a stage of their growth which can include the dormant form, or the microbial insecticides may be entrapped in association with their culture media, or the microorganism may have undergone partial or total lysis, or used partially or totally as spores, or the insecticidal products of such microorganisms can be entrapped. These microbial products having insecticidal activity can include products spontaneously excreted by the organisms such as exotoxins, or products derived from these organisms such as endotoxins, or products liberated by the organisms at certain stages of their evolution (crystals, associated or not associated to spores) or finally as several of the forms simultaneously. Good results can be obtained with insecticides comprising a mixture containing spores, associated crystals and exotoxins. Such mixtures may contain, in addition to spores, crystals related or unrelated to the spores, exotoxins, cells, debris from the cells as well as residual solids from the nutrient media in the culture.

Depending upon the end use of the insecticidal composition, the compositions of the present invention can also contain one or more conventional additives employed in insecticidal compositions. For example, ultraviolet light (UV) stabilizers such as carbon black, para-aminobenzoic acid (PABA), and the like can be added to the compositions to protect the polymer and/or the insecticide from UV degradation. Also, phagostimulants such as yeast can be incorporated into the compositions. In addition, fillers can be added to the compositions to facilitate break up of the compositions and thus allow easier access to the active insecticide. Furthermore, fillers can be added to the composition to improve storage, flowability, or to facilitate application to the insects' environment. The filler can be organic or inorganic or mixtures thereof.

Mineral or inorganic fillers can be silica based, alumina or carbonates such as aluminates, precipitated silica, bentonite, attapulgite, pyrophilite, talc, kaolin, diatomaceous earth, synthetic silicates, celite, vermiculite, ground silica, hollow glass microspheres, sand, clay, chalk, calcium carbonate, or mixtures of two or more of the fillers.

Organic fillers can be lactose, starch, flours, plant matter, polymers (such as hollow polymeric microspheres), waxes or grains.

The compositions of the present invention may contain various other conventional additives. They can contain fragrances or odor masking agents or preservatives such as, antioxidants, bactericides, and bacteriostats. The compositions of the present invention can also contain contact insecticides such as, for example, chlorpyrifos (i.e., O,O-diethyl O-(3,5,6-trichloro-2-pyridyl)phosphorothioate).

Other additives can be incorporated into the compositions such as flocculants, for example, flocculants which remove competing particles and silt from an aquatic feeding zone.

It is contemplated that mixtures of any of the additives described herein may also be incorporated into the compositions of the present invention.

The compositions of the present invention can also be coated onto larger carrier particles (among these, ground corn cobs, and the like) for ease of application.

It is also contemplated that the insecticidal compositions of the present invention can be mixed with other insecticidal compositions including nonentrapped ingestible biological insecticides in order to achieve an initial high level of insecticidal activity which is followed by a sustained level of activity due to the entrapped materials.

The concentration of any additives in the compositions can vary. Generally, the additives or mixture of additives are present in an amount of from about 0.05 percent to about 99 percent by weight, based on the total weight of the entire composition, and preferably between about 0.5 percent and about 95 percent by weight.

The entrapped compositions formed by the process of the present invention can have varying physical dimensions, however, they usually are particles larger than about 1 micrometer (μm), but are small enough to permit ingestion by the target insect, and preferably are between about 1 μm and 100 μm in diameter and more preferably between about 10 μm and about 50 μm in diameter. If the compositions formed by the process of the present invention contain particles larger than 100 μm, they can easily be made into more desired smaller particles by using mild physical or mechanical means well known in the art.

The compositions of the present invention can be formulated with buffers to increase the pH stability of the insecticide in the application zone, for example, on a leaf surface which itself may be very basic or very acidic. The compositions of the present invention can also be formulated, as known in the art, to provide increased stability of the composition toward enzymes that may be present in the application zone. In addition, the compositions of the present invention can be formulated in such a way, as known in the art, so that the insecticide is released from the polymer matrix under specified conditions, such as, for example, under conditions present in the gut or digestive tract of the target insect.

In a preferred embodiment of the present invention, a composition of Bti entrapped in an ethylene and acrylic acid copolymer is ingested by a mosquito larva. Although not to be bound by any particular mode of action, it is believed that the environment within the gut of the larva, generally an alkaline environment, causes the polymer charge to become further modified, thereby releasing the Bti from the polymer matrix. The released Bti then exhibits its insecticidal effect upon the larva. Alternatively, the polymer matrix may swell in the gut to allow alkaline digestive juices, including proteases, to enter the polymer matrix. The alkaline digestive juices may also swell the polymer matrix itself thereby exposing the insecticide.

After the compositions of the present invention are formed according to the methods disclosed herein, it may be desirable to further modify the charge of the composition in order to control or tailor its water or pH sensitivity to optimize its characteristics for a given target insect and/or make it more or less responsive to the pH or ionic strength of the surrounding environment. This further modification can be accomplished by adding or incorporating additional charged polymer (i.e., incorporating more unmodified polymer) to the composition or by adding an appropriate acid, base, or salt to the composition.

In preferred compositions of the present invention, the polymer imparts sufficient hydrophobicity or sufficient density modification (or both) to the insecticidal compositions such that the composition has a higher water flotation ability, as compared to the insecticide alone (i.e., as compared to the nonentrapped insecticide). This higher flotation ability is particularly advantageous when the target insects are mosquito larvae. The preferred insecticidal composition, because of its higher flotation ability, will remain in the feeding zone of the mosquito larvae longer, and thus, be more efficacious than non-entrapped insecticide. The feeding zone of mosquito larvae will vary from species to species; however, typically the feeding zone is about the upper 10 to 40 centimeters of aquatic environments such as lakes, ponds, pools, salt marshes, and the like.

In other embodiments of the present invention it may be advantageous to formulate the compositions to have a lower water flotation ability. For example, for target insects whose feeding zones are not limited to the upper portions of the aquatic environment (e.g., black fly larvae), it may be desirable, for specific uses, to have compositions of a buoyancy such that the compositions are substantially distributed throughout the aquatic environment. As can be seen, the present compositions can be easily tailored to provide final compositions to match the specific desired uses of the compositions.

The invention also relates to the use of the compositions of the present inventions insecticides, preferably to destroy insects. In order to control susceptible insects, the compositions are applied to the habitats of the target insect according to known techniques. Such applications can be accomplished mechanically, by air, or by other means known in the art. The compositions can be distributed in areas infested by target insects such as in areas infested by insects of the *Lepidoptera, Diptera, Coleoptera, Orthoptera, Isoptera* or *Homoptera* orders.

The insecticidally effective amount will vary widely with the type of insecticide employed. For example, if the insecticide is a virus, the effective amount can be very small; whereas if the insecticide is the toxic product of bacterium, the effective amount can be relatively large. However, a typical insecticidally effective amount of ingestible insecticide present in the compositions of the present invention is from about 0.001 percent to about 95 percent by weight of the insecticide to the total weight of the polymer and insecticide; preferably from about 0.01 percent to about 75 percent; and most preferably from about 0.1 percent to about 50 percent.

The dosages to be used will be determined by, among other things, the insecticide in question, the target insect to be eliminated and the method of application. Typical dosages are about 0.01 to about 10 kilograms of insecticidal composition solids per hectare. In the case of Bt and Bti, about 0.05 to 5 kilograms (kg) of insecticidal composition solids per hectare are typically used.

The present invention is further illustrated by the following examples; however, these examples should not be interpreted as a limitation upon the scope of the present invention. All percentages are by weight, unless otherwise indicated.

EXAMPLE 1

Bti wettable powder (that is, a powder containing crystals and spores of *Bacillus thuringiensis* var. *israelensis*) was added to water to achieve a 0.18 percent by weight aqueous Bti dispersion. NaOH was added to the dispersion to adjust the pH to 8.0. An alkaline (about pH 8) aqueous dispersion of ethylene and acrylic acid copolymer (the copolymer containing between about 15 and 20 percent acrylic acid by weight and is commercially available from The Dow Chemical Company, Midland, Mich., and known by the trademarks Primacor® 4990 or Primacor® 4983) was added to the Bti dispersion to achieve a 1 percent by weight concentration of polymer. After the polymer addition, 0.1N HCl was slowly added to the dispersion while mixing until the pH was 3.5 which modified the charge of the polymer thereby causing precipitation of the polymer with the Bti entrapped in the polymer matrix. The resulting solid was then filtered, air dried and ground to a particle size of between about 1 and 100 µm.

EXAMPLE 2

Various charged polymers were investigated for their ability to entrap Bti during precipitation. The polymers were precipitated by pH change, addition of divalent ions, or salting out with simple salts. For anionic polymers, 1N HCl, 7.5M $CaCl_2$ or 5N NaCl was added to the polymer solutions (or polymer dispersions in the case of the polymers containing phosphinic or phosphonic acid moieties). For the cationic polymers, 1N NaOH, or 1N $H_2SO_4$ was added. A coacervation reaction was also done for each of the polymers; a polymer of acrylic acid monomer was mixed with cationic polymers and a polymer of diallyldimethylammonium chloride monomers was mixed with the anionic polymers. If precipitation occurred, the process was repeated in the presence of Bti. Results are shown in Table 1. Efficiency of Bti entrapment was estimated by microscopic examination. In the microscopic examination, Bti which is entrapped is seen in association with the polymeric material rather than free of the polymeric material. The values assigned for the degree of entrapment are shown in Table 2. The numerical values in Table 2 (i.e., 0 to 100) represent the percent efficiency of entrapment. A value of 0 means that none of the Bti was observed to be entrapped and a value of 100 means that all of the Bti was observed to be entrapped. In these experiments, a composition with a value of 100 contains approximately 50 percent Bti by weight.

TABLE 1

RESULTS OF PRECIPITATION AND BTI ENTRAPMENT STUDIES OF VARIOUS POLYMERS

| Polymer/source | Method of Precipitation: | | | |
| --- | --- | --- | --- | --- |
| | pH Change | Divalent Ion Addition | Salting Out | Coacervation |
| ANIONIC | HCl | $CaCl_2$ | NaCl | |
| poly(acrylic acid) linear | —* | +/+** | +/+ | +/+ |
| poly(acrylic acid) cross-linked | — | +/+ | +/+ | +/+ |
| carrageenan, IV | — | — | — | +/+ |
| carrageenan, V | — | — | — | +/+ |
| poly(styrenesulfonate) | — | +/+ | — | +/+ |
| polymeric latex of styrene and butadiene with phosphinic acid moieties | +/+ | +/+ | — | +/+ |
| polymeric latex of styrene and butadiene with phosphonic acid moieties | — | +/+ | — | +/+ |
| ethylene and acrylic acid copolymer (about 20% acrylic acid) | +/+ | +/+ | +/+ | +/+ |
| CATIONIC | NaOH | $H_2SO_4$ | | |
| poly(diallyldimethylammonium chloride) | — | — | NT | +/+ |
| poly(vinylbenzyltrimethyl ammoniumchloride) | — | — | NT | +/+ |
| JR-400 (a cationic derivative of hydroxyethyl cellulose) | — | — | NT | +/+ |
| polybrene ionene | — | — | NT | +/+ |
| poly(ethylenimine) | — | +/–*** | NT | +/+ |
| reactive polysoap | — | +/+ | NT | +/+ |

*"—" = precipitation of polymer did not occur
**"+/+" = precipitation of polymer occurred and Bti was entrapped
***"+/–" = precipitation of polymer occurred and Bti was not entrapped
NT means no test was performed
JR 400 represents UCARE® polymer JR-400, a registered trademark of Union Carbide Corporation U.S.A.

TABLE 2

PERCENT EFFICIENCY OF BTI ENTRAPMENT STUDIES OF VARIOUS POLYMERS

| Polymer/source | Method of Precipitation: | | | |
|---|---|---|---|---|
| | pH Change | Divalent Ion Addition | Salting Out | Coacervation |
| ANIONIC | | | | |
| poly(acrylic acid), linear | NP* | 100 | 100 | 100 |
| poly(acrylic acid), cross-linked | NP | 100 | 100 | 100 |
| carrageenan, IV | NP | NP | NP | 65 |
| carrageenan, V | NP | NP | NP | 60 |
| poly(styrenesulfonate) | NP | 20 | NP | 100 |
| polymeric latex of styrene and butadiene with phosphinic acid moieties | 80 | 90 | NP | 95 |
| polymeric latex of styrene and butadiene with phosphonic acid moieties | NP | 100 | NP | 95 |
| ethylene-acrylic acid copolymer(about 20% acrylic acid) | 100 | 100 | 99 | 100 |
| CATIONIC | | | | |
| poly(diallyldimethylammonium chloride) | NP | NP | NT** | 100 |
| poly(vinylbenzyltrimethyl ammoniumchloride) | NP | NP | NT | 75 |
| JR-400 (a cationic derivative of hydroxyethyl cellulose) | NP | NP | NT | 100 |
| polybrene ionene | NP | NP | NT | 100 |
| poly(ethylenimine) | NP | 0 | NT | 80 |
| reactive polysoap | NP | 70 | NT | 90 |

*NP = No precipitation of polymer (corresponds to the "—" designation employed in Table 1).
**NT means no test was performed.

EXAMPLE 3

Various charged copolymers and multipolymers were tested for their ability to entrap Bti during precipitation by a pH change (the addition of 0.1N HCl) or by divalent ion addition (the addition of $CaCl_2$). The methods used were substantially as described in Example 2. The results are shown below in Table 3.

TABLE 3

PERCENT EFFICIENCY OF BTI ENTRAPMENT STUDIES OF VARIOUS POLYMERS

| Polymer** | Method of Precipitation: pH Change | Divalent Ion Addition |
|---|---|---|
| 50 MAA/50 EA | 100 | NP* |
| 40 MAA/60 BA | 100 | 100 |
| 60 MAA/40 ST | 90 | 90 |
| 60 MAA/40 BD | 100 | 100 |
| 20 AA/80 EL | 100 | 100 |
| 50 AA/50 AM | 100 | 100 |
| 50 EA/30 VAc/10 MAA/10 AA | 100 | NP |
| 56 MMA/20 MAA/20 EA | 99 | 80 |
| 56 MMA/20 MAA/24 EA | 100 | 85 |

*NP = No precipitation occurred;
**MAA = methacrylic acid;
BA = butyl acrylate;
BD = butadiene;
EL = ethylene;
VAc = vinyl acetate;
EA = ethyl acrylate;

TABLE 3-continued

PERCENT EFFICIENCY OF BTI ENTRAPMENT STUDIES OF VARIOUS POLYMERS

| Polymer** | Method of Precipitation: pH Change | Divalent Ion Addition |
|---|---|---|

ST = styrene;
AA = acrylic acid;
AM = acrylamide;
MMA = methyl methacrylate.

The number preceding the polymer component indicates the approximate percent by weight of that component in the polymer, e.g., 50 MAA/50 EA represents a polymer composed of about 50 percent by weight of methacrylic acid and 50 percent by weight of ethyl acrylate.

EXAMPLE 4

Persistence of the compositions of the invention in the mosquito feeding zone was demonstrated by the following. A 4 milligram (mg) sample of a desired insecticidal composition was prepared employing a pH change to precipitate the polymer to entrap Bti as previously described hereinabove. The insecticidal composition was 1 part ethylene and acrylic acid copolymer (EAA) (composed of about 20 percent by weight acrylic acid) to one part Bti and was applied to the surface of 500 milliliters (mL) of water contained in a separatory funnel. After 10 days, five 100 mL fractions were drained from the funnel through the stopcock.

Twenty *Aeddes egypti* larvae were placed into each fraction, surviving larvae were counted 24 hours later. Of the 5 fractions, the fraction containing the uppermost layer, in the separatory funnel, exhibited the majority of the activity, killing 100 percent of the larvae. The bottom fraction had slight activity and no activity was found in the other fractions.

EXAMPLE 5

The following test was conducted to determine the UV protection obtained for the microorganisms by the addition of UV absorbers to a polymer. *Escherichia coli* was chosen for this test, even though this bacteria, in its normal form, is not useful in the present invention, but because this bacteria dies when it is exposed to UV radiation, the results when using *Escherichia coli* are indicative of the results which would be obtained with the microorganisms of the present invention.

Films were cast from an alkaline (about pH 8) dispersion of EAA (Primacot® 4990) using standard procedures known in the art. UV absorbers such as carbon black and para-aminobenzoic acid (PABA) were incorporated into the dispersion before casting. These films were used to shield plates of agar inoculated with *Escherichia coli* (strain JC411) during exposure to a germicidal lamp placed 14 inches above the plates. After exposure, plates were incubated for 24 hours and surviving *Escherichia coli* colonies were counted. The EAA film without UV absorbers gave no significant protection to plates exposed for 30 seconds. Incorporating carbon black into the film at a concentration of 3 percent protected 30 percent of the bacteria from 3 to 10 minutes exposure and 15 percent of the bacteria from 15 minutes exposure. PABA incorporated into the film at a concentration of 3 percent gave 100 percent protection of the bacteria and at a 2 percent concentration gave 50 percent protection in testing employing 15 minutes of UV exposure.

EXAMPLE 6

The following example illustrates the incorporation of carbon black into a insecticidal composition.

Carbon black (0.15 g) was added to 14.28 grams (g) of a 33 percent alkaline (about pH 8) aqueous dispersion of ethylene and acrylic acid copolymer (about 20 percent by weight acrylic acid). The resulting ethylene and acrylic acid copolymer/carbon black mixture was then added to 500 mL of a 1 percent aqueous suspension of Bti. The carbon black was well dispersed and 100 percent incorporation of the carbon black into the insecticidal composition was achieved upon precipitation using 0.1N HCl.

EXAMPLE 7

The following example illustrates the preparation of a polymer dispersion containing about 35 percent solids.

The following components were mixed together in a one gallon stirred batch reactor at ambient temperature. The components were added to the batch reactor in the following order.

(1) 760 grams ethylene and acrylic acid copolymer (about 20 percent acrylic acid, 1100 melt index)

(2) 1350 grams deionized water (3) 60 milliliters $NH_3$ in water to make a $NH_3$:COOH mole ratio of 0.35:1.0.

After the components were added, the reactor was heated, with continuous stirring, to 110° C. and held at that temperature for 1.5 hours. The stirred mixture was allowed to cool to 35° C. before it was discharged from the reactor. The dispersion was filtered through a 100 mesh screen, and allowed to cool to ambient temperature.

EXAMPLE 8

A dispersion containing 12.45 g Bti technical powder (powder containing crystals and spores of *Bacillus thuringiensis* var. *israelensis*), 12.45 g ethylene and acrylic acid copolymer solids (EAA) (PRIMACOR® 4990), and 0.09 g PVDC microspheres (polyvinylidene chloride), (MIRALITE® 177) was prepared in 1200 ml water. Acid precipitation was achieved by the addition of 0.1N HCl until the pH 3.5 which modified the charge of the polymer causing precipitation of the polymer with the Bti and PVDC microspheres entrapped in the polymer matrix. The resulting solid was then filtered and dried under agitation in a laboratory scale Hobart mixer using a wire wisp attachment. After 8 hours of drying time, the result was a fine powder in which the diameter of the majority of particles was between 1 and 100 μm. Examination with a phase contrast microscope revealed that Bti/EAA material adhered to the surface of the hollow microspheres.

EXAMPLE 9

A package (7 g) of Fleischmann's Active Dry yeast was added to 60 ml of water at 40° C. This mixture was stirred with a magnetic stirring bar and held for 30 minutes at this temperature. The mixture was then added to a dispersion containing Bti wettable powder (powder containing crystals and spores of *Bacillus thuringiensis* var. *israeiensis*) and EAA (PRIMACOR® 4990), each at a concentration of 1 percent solids by weight. The total volume of the mixture after all components had been added was 1254 mL. Precipitation of the EAA was achieved by the addition of 0.1N HCl while mixing, until the pH was 3.5, which modified the charge of the polymer thereby causing precipitation of the polymer with the Bti and the yeast entrapped in the polymer matrix. The resulting solid was then filtered, air dried and ground to a particle size of between 1 and 100 μm.

We claim:

1. An ingestible biological insecticidal composition comprising an insecticidally effective amount of an ingestible biological insecticide selected from the group consisting of DNA viruses, RNA viruses, bacteria of the genus *Bacillus* and the insecticidally active products of such bacteria entrapped by a precipitated charged polymer, said composition further comprising an ultraviolet light stabilizer; and said composition being prepared by a process which comprises contacting the ingestible biological insecticide with the ultraviolet light stabilizer and a charged polymer in an aqueous medium, and then, in said medium, modifying the charge of a sufficient quantity of the functional groups of the charged polymer by adding a precipitant to the aqueous medium selected from the group consisting of an acid to raise the pH, a base to lower the pH, a salt to cause salting out, and multivalent ions of a charge opposite to the charge of the charged polymer to cause precipitation of the polymer and entrapment of the insecticide.

2. The composition as defined in claim 1 wherein the insecticide is present in an amount of from about 0.001 percent to about 95 percent by weight and the polymer is present in an amount of from about 99.999 percent to about 5 percent by weight, based on the total weight of the insecticide and polymer.

3. The composition as defined in claim 2 wherein the insecticide is present in an amount of from about 0.001 percent to about 75 percent by weight and the polymer is present in an amount of from about 99.999 percent to about 25 percent by weight, based on the total weight of the insecticide and polymer.

4. The composition as defined in claim 3 wherein the insecticide is present in an amount of from about 0.1 percent to about 50 percent by weight and the polymer is present in an amount of from about 99.9 percent to about 50 percent by weight, based on the total weight of the insecticide and polymer.

5. The composition as defined in claim 1 wherein the insecticide is a DNA virus.

6. The composition as defined in claim 5 wherein the DNA virus is nuclear polyhedrosis virus.

7. The composition as defined in claim 1 wherein the insecticide is a RNA virus.

8. The composition as defined in claim 1 wherein the insecticide is a bacteria of the genus Bacillus, insecticidally toxic components thereof, insecticidally toxic products thereof, or mixtures thereof.

9. The composition as defined in claim 8 wherein the bacteria is selected from the group consisting of Bacillus thuringiensis, Bacillus sphaericus, Bacillus popilliae, Bacillus cereus, Bacillus lentimorbus and Bacillus fribourgensis.

10. The composition as defined in claim 9 wherein the bacteria is Bacillus thuringiensis.

11. The composition as defined in claim 10 wherein the bacteria is Bacillus thuringiensis var. israelensis, insecticidally toxic components thereof, insecticidally toxic products thereof, or mixtures thereof.

12. The composition as defined in claim 1 wherein the precipitated charged polymer is selected from the group consisting of polybrene ionene; carrageenan type IV; ethyleneimine polymers; vinylbenzyltrimethylammonium chloride polymers; diallyldimethylammonium chloride polymers; ethylene/acrylic acid copolymers; ethylene/methacrylic acid copolymers; linear acrylic acid polymers; cross-linked acrylic acid polymers; styrene-sulfonic acid polymers; butadiene containing phosphinic acid moieties; polymeric latexes of styrene and butadiene containing phosphonic acid moieties; copolymers of methacrylic acid and ethyl methacrylic acid/ethyl acrylate copolymers; methacrylic acid/butyl acrylate copolymers; methacrylic acid/styrene copolymers; methacrylic acid/butadiene copolymers; acrylic acid/acrylamide copolymers; ethyl acrylate/vinyl acetate/methacrylic acid/acrylic acid multipolymers; and methyl acrylate/methacrylic acid/ethyl acrylate multipolymers.

13. The composition as defined in claim 12 wherein the polymer is a copolymer of ethylene and acrylic acid or a copolymer of ethylene and methacrylic acid.

14. The insecticidal composition as defined in claim 12 comprising Bacillus thuringiensis var. israelensis entrapped by a precipitated ethylene and acrylic acid copolymer, said composition further containing an ultraviolet light stabilizer.

15. The composition as defined in claim 14 wherein the amount of acrylic acid in the copolymer represents about 12 percent to about 25 percent by weight of the copolymer.

16. The composition as defined in claim 1 further comprising an inorganic filler.

17. The composition as defined in claim 16 wherein the filler is a hollow glass microsphere.

18. The composition as defined in claim 1 further comprising an organic filler.

19. The composition as defined in claim 18 wherein the filler is a hollow polymeric microsphere.

20. The composition as defined in claim 1 wherein said composition is in the form of particles between about 1 µm and 100 µm in diameter.

21. The composition as defined in claim 20 wherein said composition is in the form of particles between about 10 µm and 50 µm in diameter.

22. A process for the preparation of ingestible biological insecticidal compositions which comprises contacting an ingestible biological insecticide selected from the group consisting of DNA viruses, RNA viruses, bacteria of the genus Bacillus and the insecticidally active products of such bacteria with an ultraviolet light stabilizer and a charged polymer in an aqueous medium, and then, in said medium, modifying the charge of a sufficient quantity of the functional groups of the charged polymer by adding a precipitant to the aqueous medium selected from the group consisting of an acid to raise the pH, a base to lower the pH, a salt to cause salting out, and multivalent ions of a charge opposite to the charge of the charged polymer to cause precipitation of the polymer and entrapment of the insecticide to form a solid insecticidal composition comprised of an in insecticidally effective amount of the ingestible biological insecticide entrapped by a precipitated charged polymer.

23. The process as defined in claim 22 wherein the insecticide is present in an amount of from about 0.001 percent to about 95 percent by weight and the polymer is present in an amount of from about 99.999 percent to about 5 percent by weight, based on the total weight of the insecticide and polymer.

24. The process as defined in claim 22 wherein the insecticide is present in an amount of from about 0.001 percent to about 75 percent by weight and the polymer is present in an amount of from about 99.999 percent to about 25 percent by weight, based on the total weight of the insecticide and polymer.

25. The process as defined in claim 22 wherein the insecticide is present in an amount of from about 0.1 percent to about 50 percent by weight and the polymer is present in an amount of from about 99.9 percent to about 50 percent by weight, based on the total weight of the insecticide and polymer.

26. The process as defined in claim 22 wherein the insecticide is a DNA virus.

27. The process as defined in claim 25 wherein the DNA virus is nuclear polyhedrosis virus.

28. The process as defined in claim 22 wherein the insecticide is a RNA virus.

29. The process as defined in claim 22 wherein the insecticide is a bacteria of the genus Bacillus, insecticidally toxic components thereof, insecticidally toxic products thereof, or mixtures thereof.

30. The process as defined in claim 29 wherein the bacteria is selected from the group consisting of Bacillus thuringiensis, Bacillus sphaericus, Bacillus popilliae, Bacillus cereus, Bacillus lentimorbus and Bacillus fribourgensis.

31. The process as defined in claim 30 wherein the bacteria is Bacillus thuringiensis.

32. The process as defined in claim 31 wherein the bacteria is Bacillus thuringiensis var. israelensis, insecticidally toxic components thereof, insecticidally toxic products thereof, or mixtures thereof.

33. The process as defined in claim 22 wherein the polymer is selected from the group consisting of polybrene ionene; carrageenan type IV; ethyleneimine polymers; vinylbenzyltrimethylammonium chloride polymers; diallyldimethylammonium chloride polymers; ethylene/acrylic acid copolymers; ethylene/methacrylic acid copolymers; linear acrylic acid polymers; cross-linked acrylic acid polymers; styrenesulfonic acid polymers; methacrylic acid/ethyl acrylate copolymers; methacrylic acid/butyl acrylate copolymers; methacrylic acid/styrene copolymers; methacrylic acid/butadiene copolymers; acrylic acid/acrylamide copolymers; ethyl acrylate/vinyl acetate/methacrylic acid/acrylic acid multipolymers; and methyl acrylate/methacrylic acid/ethyl acrylate multipolymers.

34. The process as defined in claim 22 wherein the polymer is a copolymer of ethylene and acrylic acid or a copolymer of ethylene and methacrylic acid.

35. The process as defined in claim 22 wherein the modification of the charge of the functional groups of the charged polymer to effect precipitation of the polymer is accomplished by adding to the aqueous medium a precipitant selected from the group consisting of a) an acid to raise the pH;

b) a base to lower the pH;

c) a salt to cause salting out; and d) multivalent ions of a charge opposite to the charge of the charged polymer.

36. The method as defined in claim 22 said composition further comprising an inorganic filler.

37. The process defined in claim 36 wherein the filler is a hollow glass microsphere.

38. The method as defined in claim 22 said composition further comprising an organic filler.

39. The process as defined in claim 38 wherein the filler is a hollow polymeric microsphere.

40. The process as defined in claim 22 wherein the precipitated composition is in the form of particles between about 1 µm and 100 µm in diameter.

41. The process as defined in claim 40 wherein the precipitated composition is in the form of particles between about 10 µm and 50 µm in diameter.

42. A method for the control of insects which comprises applying to the habitat of said insects an insecticidally effective amount of a composition comprising an ingestible biological insecticide selected from the group consisting of DNA viruses, RNA viruses, bacteria of the genus *Bacillus* and the insecticidally active products of such bacteria entrapped by a precipitated charged polymer, said composition further comprising an ultraviolet light stabilizer; and said composition being prepared by a process which comprises contacting the ingestible biological insecticide with the ultraviolet light stabilizer and a charged polymer in an aqueous medium, and then, in said medium, modifying the charge of a sufficient quantity of the functional groups of the charged polymer by adding a precipitant to the aqueous medium selected from the group consisting of an acid to raise the pH, a base to lower the pH, a salt to cause salting out, and multivalent ions of a charge opposite to the charge of the charged polymer to cause precipitation of the polymer and entrapment of the insecticide.

43. The method as defined in claim 42 wherein the insecticide is present in an amount of from about 0.001 percent to about 95 percent by weight and the polymer is present in an amount of from about 99.999 percent to about 5 percent by weight, based on the total weight of the insecticide and polymer.

44. The method as defined in claim 43 wherein the insecticide is present in an amount of from about 0.001 percent to about 75 percent by weight and the polymer is present in an amount of from about 99.999 percent to about 25 percent by weight, based on the total weight of the insecticide and polymer.

45. The method as defined in claim 43 wherein the insecticide is present in an amount of from about 0.1 percent to about 50 percent by weight and the polymer is present in an amount of from about 99.9 percent to about 50 percent by weight, based on the total weight of the insecticide and polymer.

46. The method as defined in claim 42 wherein the insecticide is a DNA virus.

47. The method as defined in claim 46 wherein the DNA virus is nuclear polyhedrosis virus.

48. The method as defined in claim 42 wherein the insecticide is a RNA virus.

49. The method as defined in claim 42 wherein the insecticide is a bacteria of the genus *Bacillus*, insecticidally toxic components thereof, insecticidally toxic products thereof, or mixtures thereof.

50. The method as defined in claim 49 wherein the bacteria is selected from the group consisting of *Bacillus thuringiensis, Bacillus sphaericus, Bacillus popilliae, Bacillus cereus, Bacillus lentimorbus* and *Bacillus fribourgensis*.

51. The method as defined in claim 50 wherein the bacteria is *Bacillus thuringiensis*.

52. The method as defined in claim 51 wherein the bacteria is *Bacillus thuringiensis* var. *israelensis*, insecticidally toxic components thereof, insecticidally toxic products thereof, or mixtures thereof.

53. The method as defined in claim 42 wherein the precipitated charged polymer is selected from the group consisting of polybrene ionene; carrageenan type IV; ethyleneimine polymers; vinylbenzyltrimethylammonium chloride polymers; diallyldimethylammonium chloride polymers; ethylene/acrylic acid copolymers; ethylene/methacrylic acid copolymers; linear acrylic acid polymers; cross-linked acrylic acid polymers; styrene-sulfonic acid polymers; methacrylic acid/ethyl acrylate copolymers; methacrylic acid/butyl acrylate copolymers; methacrylic acid/styrene copolymers; methacrylic acid/butadiene copolymers; acrylic acid/acrylamide copolymers; ethyl acrylate/vinyl acetate/methacrylic acid/acrylic acid multipolymers; and methyl acrylate/methacrylic acid/ethyl acrylate multipolymers.

54. The method as defined in claim 53 wherein the polymer is a copolymer of ethylene and acrylic acid or a copolymer of ethylene and methacrylic acid.

55. The method as defined in claim 42 wherein said composition further comprises an inorganic filler.

56. The method as defined in claim 55 wherein the filler is a hollow glass microsphere.

57. The method as defined in claim 42 wherein said composition further comprises an organic filler.

58. The method as defined in claim 57 wherein the filler is a hollow polymeric microsphere.

59. The method as defined in claim 42 wherein said composition is in the form of particles between about 1 µm and 100 µm in diameter.

60. The method as defined in claim 59 wherein said composition is in the form of particles between about 10 µm and 50 µm in diameter.

61. A composition as defined in claim 1 further comprising a phagostimulant.

62. A method as defined in claim 42 wherein said composition further comprises a phagostimulant.

\* \* \* \* \*